United States Patent [19]

Froehlich

[11] Patent Number: 4,470,532
[45] Date of Patent: Sep. 11, 1984

[54] MEDICAL STAPLING DEVICE

[75] Inventor: Harold E. Froehlich, St. Anthony, Minn.

[73] Assignee: Minnesota Mining and Manufacturing Company, St. Paul, Minn.

[21] Appl. No.: 400,231

[22] Filed: Jul. 21, 1982

[51] Int. Cl.³ .............................................. B25C 5/06
[52] U.S. Cl. ................................... 227/19; 227/135; 227/136; 227/DIG. 1; 128/334 R
[58] Field of Search ............... 227/DIG. 1, 1 A–1 C, 227/19, 135–136; 128/334 R, 335, 336–337, 325; 29/243.56

[56] References Cited

U.S. PATENT DOCUMENTS

| 3,638,847 | 2/1972 | Noiles et al. ................. 227/DIG. 1 |
| 3,643,851 | 2/1972 | Green et al. |
| 3,662,939 | 5/1972 | Bryan . |
| 3,837,555 | 9/1974 | Green . |
| 3,873,016 | 3/1975 | Fishbien . |
| 4,014,492 | 3/1977 | Rothfuss . |
| 4,043,504 | 8/1977 | Hueil et al. ............................ 227/19 |
| 4,185,762 | 1/1980 | Froehlich ............................ 227/138 |
| 4,316,468 | 2/1982 | Klieman et al. ..................... 128/325 |

Primary Examiner—C. Fred Rosenbaum
Assistant Examiner—Gene B. Kartchner
Attorney, Agent, or Firm—Donald M. Sell; James A. Smith; William L. Huebsch

[57] ABSTRACT

A medical stapling device in which, upon activation, spaced lugs on a driver advance open staples along a track between two grooved rails frictionally holding the staples so that the leading staple will be closed around an anvil at the end of the track and can suture adjacent living tissue. Subsequently cam members which maintained the lugs in engagement with the staples as the lead staple was closed are biased by a spring to a position at which the lugs separate from and move around the staples as the driver is returned to its original position at which the lugs again engage subsequent staples along the track.

7 Claims, 12 Drawing Figures

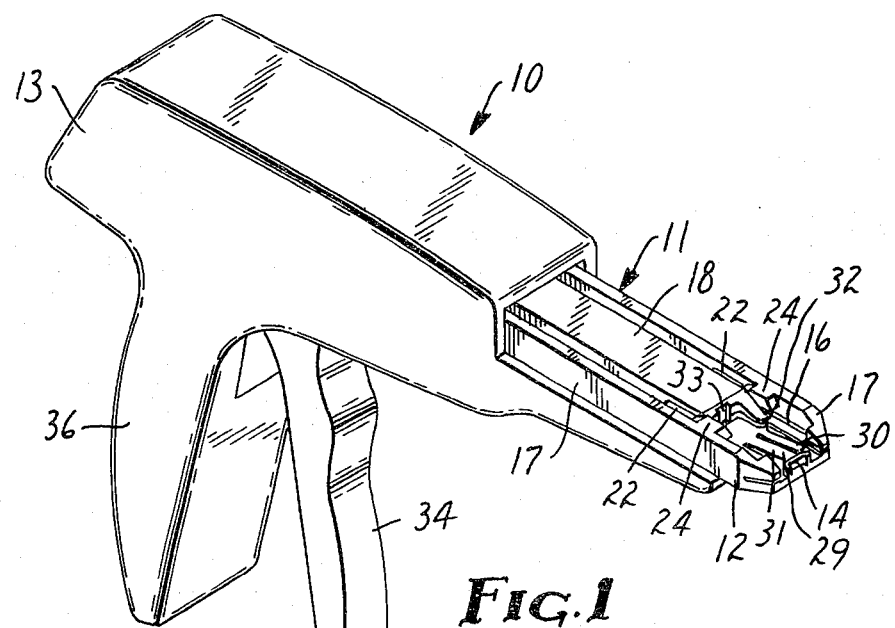
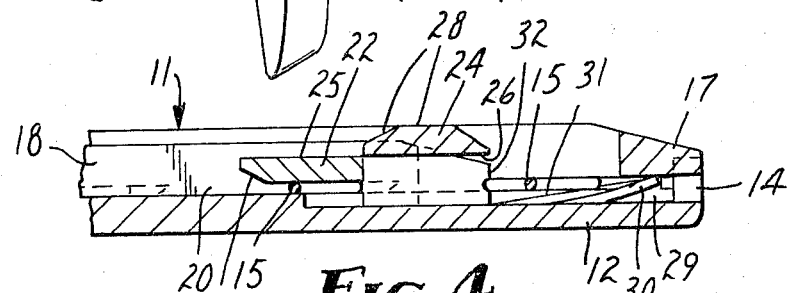
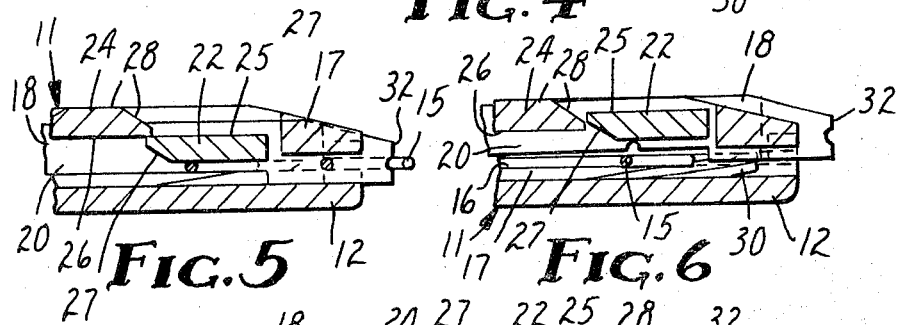
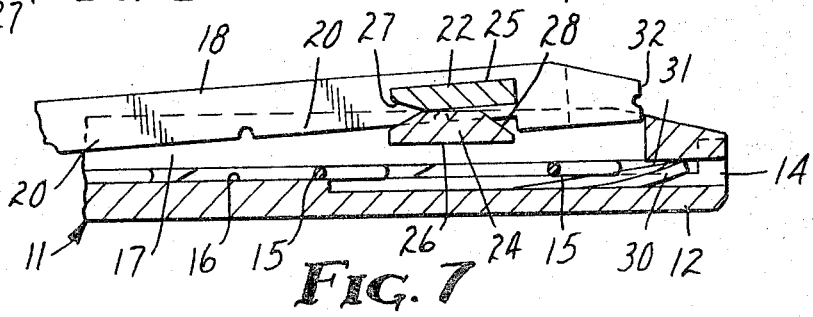

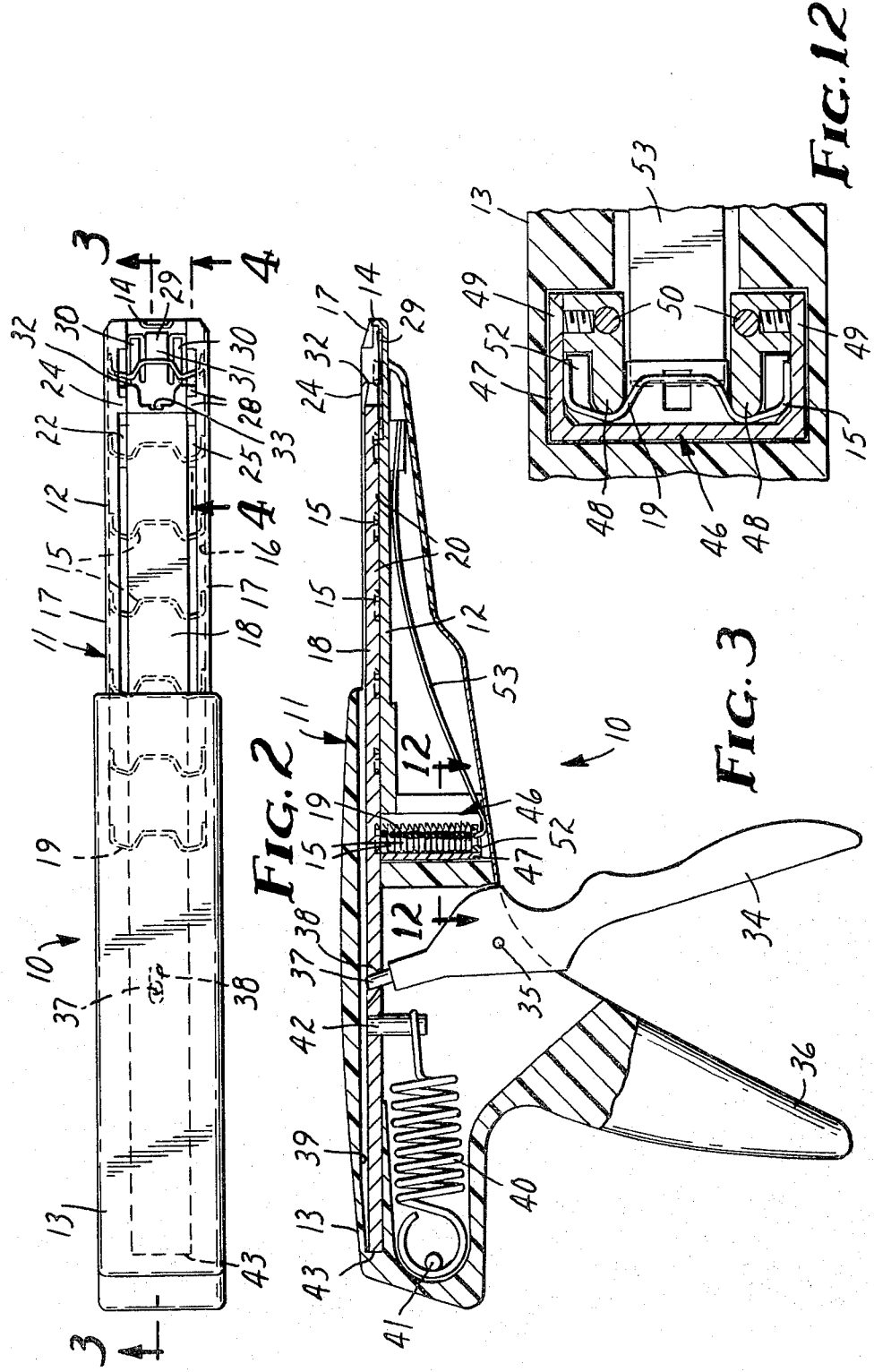

MEDICAL STAPLING DEVICE

BACKGROUND OF THE INVENTION

The present invention relates to medical stapling devices for applying metal staples to suture living tissue such as disunited skin or fascia.

The prior art is replete with medical stapling devices for use in suturing living tissues. U.S. Pat. Nos. 3,643,851; 3,662,939; 3,837,555; 3,873,016; 4,014,492 and 4,185,762 are illustrative of such devices which include various mechanisms which may be operated to move a plurality of open staples along a track and sequentially into engagement with an anvil so that the staple engaging the anvil will be closed to engage it with tissues adjacent the anvil.

The mechanisms by which these stapling devices are operated vary considerably in complexity. Simple reliable operating mechanisms are much desired in such devices to afford low manufacturing costs for the devices whether they are reusable or intended for a single use; and, where the device is reusable, so that the mechanism can be easily disassembled, cleaned, reassembled and sterilized.

SUMMARY OF THE INVENTION

The present invention provides a very simple medical stapling device which can reliably insert a series of metal staples adapted to enter living tissues.

The stapling device is of the known type including a frame, an anvil mounted in a fixed position relative to the frame, and means for moving a plurality of open staples along a track leading to the anvil and sequentially into engagement with the anvil to close the staple engaging the anvil, which means comprises a driver mounted on the frame for movement along a predetermined path generally aligned with the track between first and second positions with the driver more closely adjacent the anvil in its second position. In the improved stapling device according to the present invention, the driver includes a plurality of spaced lugs adapted to engage staples spaced at predetermined distances along the track; and the stapler includes means adapted for engagement between the driver and the frame, including cam members on the driver and on the frame that directly interact with each other, for affording positioning of the lugs in engagement with staples spaced along the track when the driver is in its first position, for causing the driver to move the staples along the track and engage the leading staple with the anvil to close the leading staple during movement of the driver from its first to its second position, and for causing movement of the lugs out of engagement with the staples along the track, around, and into engagement with subsequent staples along the track during movement of the driver from its second position back to its first position.

In the embodiment of the invention described herein the means adapted for engagement between the driver and the frame comprises (1) the cam members on the driver and the frame which have first surfaces shaped to engage and cause movement of the driver along the track with the lugs in engagement with the staples during movement of the driver from its first to its second position, which cam members also have opposite second surfaces shaped so that, upon displacement of the driver a small distance transversely away from the track at the second position of the driver and movement of the driver from its second to its first position, the second surfaces of the cam members will engage and move the driver around the staples along the track and then back to the track with the lugs in engagement with the subsequent staples along the track; and (2) spring means between the frame and the driver for displacing the cam members said small distance when the driver is in its second position.

Also in the embodiment described herein the stapling device further includes means for storing a stack of the staples in side-by-side relationship and for feeding the stack of staples to the end of the track opposite the anvil with the staple in the stack at the rails opening toward the anvil, which means significantly increases the staple capacity of the stapling device.

BRIEF DESCRIPTION OF THE DRAWING

The present invention, including various additional novel features, will be further described with reference to the accompanying drawing where like numbers refer to like parts in the several views, and wherein:

FIG. 1 is a perspective view of a stapling device according to the present invention;

FIG. 2 is a top view of the stapling device of FIG. 1;

FIG. 3 is a sectional view taken approximately along the line 3—3 of FIG. 2 and showing a normal position of a driver in the stapling device;

FIGS. 4, 5, 6 and 7 are fragmentary enlarged sectional views taken approximately along the line 3—3 of FIG. 2 which show sequential positions to which the driver is moved during the application of a staple.

FIG. 12 is an enlarged fragmentary sectional view taken approximately along line 12—12 of FIG. 3.

DESCRIPTION OF THE PREFERRED EMBODIMENT

Figure 8:
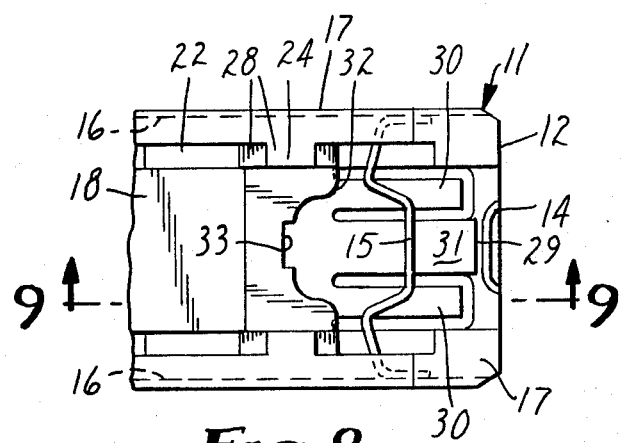
FIG. 8 is an enlarged fragmentary top view of the stapling device of FIG. 1 showing the driver in a first unactivated position.
Figure 9:
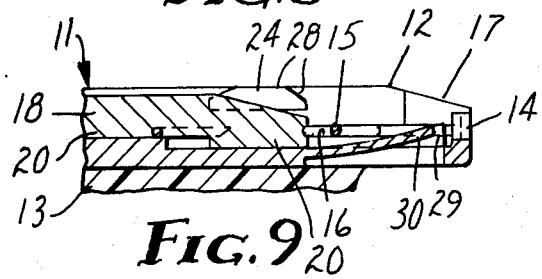
FIG. 9 is a fragmentary sectional view taken approximately along line 9—9 of FIG. 8.

Referring now to the drawing there is shown a stapling device or stapler according to the present invention, generally designated by the numeral 10.

The stapling device 10 includes a frame 11 comprising a metal (e.g., stainless steel) guide plate 12 fixed within a two-part housing 13 of a polymeric material, an anvil 14 fixed on one end of the guide plate 12, and means for moving a plurality of open staples 15 along a track 16 defined on the guide plate 12 leading to the anvil 14 and sequentially into engagement with the anvil 14 to close the leading staple 15 by engagement with the anvil 14 (FIGS. 5, 6 and 10) so that the closed staple 15 may suture living tissues (such as disunited skin or fascia) adjacent the anvil 14.

Figure 10:
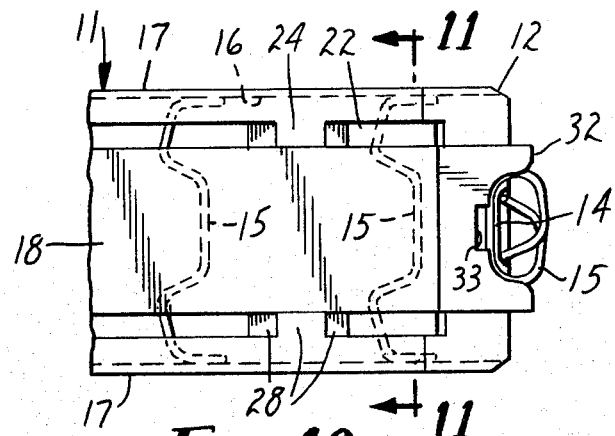
FIG. 10 is a fragmentary top view similar to FIG. 8, but which shows the driver in a second activated position at which it has closed a staple.
Figure 11:
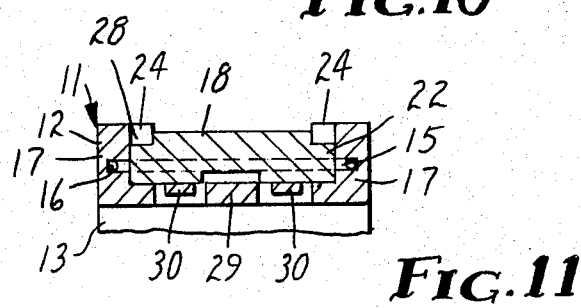
FIG. 11 is a sectional view taken approximately along line 11—11 of FIG. 10.

As is best seen in FIG. 11, the track 16 is defined by parallel elongate rails 17 formed on the guide plate 12 and having opposed grooves in which end portions of the staples 15 are frictionally received with the staples 15 opening toward the anvil 14. The rails 17 are adapted so that the staples 15 can be frictionally slid along the rails 17 to the anvil 14 from inlet ends of the rails 17 opposite the anvil 14, to which inlet ends staples 15 are fed seriatim from a stack 19 of the staples 15 (FIG. 3) by means to be explained later. The means for moving the open staples 15 along the track 16 includes an elongate metal driver 18 guided between the rails 17 for movement along a predetermined path generally aligned with the track 16 between a first position (FIGS. 2, 4 and 8) and a second position (FIGS. 6 and 10) with the driver 18 more closely adjacent the anvil 14 in its second position. The driver 18 includes a plurality of spaced lugs 20 adapted to engage between staples 15 spaced at predetermined distances along the rails 17 through an opening between the rails 17. The stapler 10 includes means adapted for engagement between the driver 18 and the frame 11 for affording positioning of the lugs 20 in engagement with staples 15 spaced at said predetermined distances along the rails 17 when the driver 18 is in its first position and for causing the driver 18 to advance the staples 15 along the rails 17 and engage the leading staple 15 with the anvil 14 (FIG. 5) to close the leading staple 15 around the anvil 14 as the driver 18 reaches the second position, and for then causing movement of the lugs 20 out of engagement with the staples 15 along with rails 17 (FIG. 6), around (FIG. 7), and then back into engagement with subsequent staples 15 spaced along the rails 17 during movement of the driver 18 from its second position (FIGS. 6 and 10) back to its first position (FIGS. 2, 4 and 8).

As illustrated, the means adapted for engagement between the driver 18 and the frame 11 comprises cam members 22 and 24 fixed on the driver 18 and on the guide plate 12 respectively with the cam members 22 projecting transversely outwardly from the driver, and the cam members 24 projecting toward each other from the rails 17. The cam members 22 and 24 have peripheral surface portions adapted for engagement during various portions of the driver's 18 movement, including planar portions 25 and 26 adapted to engage and insure movement of the driver 18 along the track 16 with the lugs 20 in engagement with the staples 15 along the rails 17 during movement of the driver 18 from its first to its second position (FIG. 10). Also the cam members 22 and 24 have second surface portions 27 and 28 respectively opposite the planar surface portions 25 and 26 shaped to engage and move the driver 18 around the staples 15 along the rails 17 (FIG. 7) and then back to a position with the lugs 20 in engagement with subsequent staples 15 along the rails 17 during movement of the driver 18 from its second to its first position, provided the cam members 22 on the driver 18 are displaced a small distance transversely away from the track 16 when the driver 18 is in its second position (FIG. 10). Such displacement is provided by two parallel cantilever lifting springs 30 formed from (as by laser cutting) and fixed at one end on the guide plate 12 in the track 16 between the cam members 24 and the anvil 14. After the driver 18 has been moved to its second position to form the leading staple 15 around the anvil 14 (FIG. 10), the lifting springs 30 will lift the end of the driver 18 adjacent the anvil 14 away from the track 16 (FIG. 6) so that the second surfaces 27 and 28 of the cam members 22 and 24 will engage (FIG. 7) to produce the result described above as the driver 18 is returned to its first position.

As illustrated, an end surface 32 of the end lug 20 on the driver 18 is specially shaped and transversely grooved to cooperate with the anvil 14 to close the staple 15 which has a special shape for suturing fascia as is described and claimed in U.S. patent application Ser. No. 248,575, filed Mar. 27, 1981, the content whereof is incorporated herein by reference. Alternatively, however, the end surface 32 and anvil 14 could be shaped to close a staple of the type described in U.S. Pat. No. 4,185,762, the content whereof is also incorporated herein by reference.

Generally, as taught in U.S. patent application Ser. No. 248,575, the staple 15 comprises a length of wire having a straight or slightly curved central portion, and arcuate end portions including straight or slightly curved terminal end parts having points on their ends opposite the central portion, with the points on the end portions and the central portion being generally aligned. The anvil 14 projects into the track 16 at approximately a right angle to a plane defined by the side surfaces of staples 15 along the rails 17. The anvil 14 has an arcuate surface adapted to be engaged by the central portion and adjacent parts of the end portions of the staple 15. The driver 18 is transversely grooved along its end surface 32 and includes spaced projections defining its end surface 32 that will engage and bend the staple 15 around the juncture between its central and end portions. Such bending will form a generally oval shape for the central portion and adjacent parts of the end portions of the staple 15 and will bring the terminal end parts of the end portions of the staple 15 into side-by-side crossed relationship with the points of each of the end portions positioned adjacent the juncture between the central portion and the other of the end portions (i.e., the terminal end parts can cross, terminate at, or terminate within the outer portions of the staple either at or outboard of the juncture; and, particularly with curved terminal end parts, could lay approximately along the other of the end portions).

As illustrated, the stapler 10 includes a block 29 projecting centrally into the track 16 that has a surface facing the anvil 14 adapted to engage the central portion of the staple 15 on its side opposite the anvil 14 to prevent if from bowing away from the anvil 14 as the staple 15 is closed. The block 29 has a ramp surface 31 over which the central portion of a staple 15 must pass as the staple 15 moves into engagement with the anvil 14. While such passage might be facilitated by movably mounting the block 29 so that it can be pressed into the guide plate 12 against the bias of a spring, it has been found that the block 29 can instead be fixed on the guide plate 12 and the central portion of the staple 15 (which central portion is unsupported across a notch 33 in the driver 18 adapted to receive the block 29 when the driver 18 is in its second position) will deflect over the ramp surface 31 and will audibly click into the slot between the block 29 and the anvil 14. It is also expected that for some staple sizes and/or shapes the block 29 and its function would not be needed at all.

The means for moving the staples 15 along the track 16 also include manually activatable means for moving the driver 18 between its first and second positions. This manually activatable means includes an activating lever 34 pivotably mounted on the frame 11 via a pin 35 with a major portion of the lever 34 projecting along a pistol-grip portion 36 of the frame 11, and a minor portion projecting into a socket 39 in the housing 13 parallel to the track 16 in which an end portion of the driver 18 opposite its end surface 32 is slidably received. That minor portion of the lever 34 terminates in a pin-like projection 37 that projects into a frustro-conical opening 38 through the driver 18 from its smallest end. The lever 34 is manually pivotal between (1) an unactivated position (FIG. 3) with the major end portion of the lever spaced from the pistol grip 36 a small distance so that the grip and lever 34 can be received in the semi-closed hand of a user with the driver 18 in its first position, to which first position the driver 18 is biased by a coil main spring 40 tensioned between a pin 41 on the frame 11 and the distal end of a pin 42 fixed to the driver 18 and projecting at right angles to the tracks 16 away from the driver 18; and an activated position adjacent the pistol grip 36 to which the major portion of the activating lever 34 can be manually pressed, and which, via the projection 37, moves the driver 18 to its second position against the bias of the main spring 40.

The main spring 40 is disposed and mounted in the stapler 10 to provide a single spring means for biasing the driver 18 to its first position and to a position with the lugs 20 in engagement with the staples 15 along the rails 17 both in the first position of the driver 18 and during movement of the driver 18 form its first position to its second position; and for biasing the second surfaces 27 and 28 of the cam members 22 and 24 into engagement with each other as the driver 18 is moved by the main spring 40 from its second position back to its first position. The elongate drive 18 has an end 43 opposite the anvil 14 guided on the guide plate 12 along a path parallel to and generally along the track 16. The cam members 22 and 24 are positioned near the end of the driver 18 adjacent the anvil 14. The pin 42 on the driver 18 is between its end 43 and the cam members 22 and 24 projects from the side of the driver 18 opposite the direction the end portion of the driver 18 adjacent the anvil 14 is displaced from the track 16 in its second position. The main spring 40 is coupled between the frame 11 and the pin 42 at an angle with respect to the driver 18 that will both bias the driver 18 to its first position and provide a torque around the end 43 of the driver 18 opposite the anvil 14 in all positions of the driver 18 to bias the driver 18 toward the track 16.

The means in the stapler 10 for storing the stack of the staples 15 in side-by-side relationship and for feeding the stack to the end of the track 16 opposite the anvil 14 is best seen in FIGS. 3 and 12. The stack 19 of the staples 15 is defined by a cartridge-like structure 46 comprising a channel 47 having a generally U-shaped cross section, and two longitudinally extending guide bars 48 fastened in spaced relationship within the channel 47 via screws 49. The stack 19 of the staples 15 is disposed between the channel 47 and the guide bars 48 which are fastened within an opening in the housing 13 by two spaced attaching bolts 50 engaged with the guide plate 12 so that the stack 19 projects downwardly generally at right angles to the rails 17. The side of the rails 17 adjacent the stack 19 has an opening which allows the top staple 15 in the stack 19 to move between the rails 17 and into alignment with the grooves in the rails 17 that frictionally receive the staples 15 along the track 16. The stack 19 of the staples 15 is biased toward the rails 17 by means comprising a cantilevered follower spring 53 having one end fastened to the guide plate 12 along its end adjacent the anvil 14, and its other end projection between the guide bars 48 and biased against a generally staple-shaped follower 52 at the end of the stack 19 opposite the rails 17. The follower spring 53 is sufficiently flexible that it may be bent away from the stack 19 to afford removal of the follower 52 and addition of staples to the stack 19. Normally, the biasing of the stack caused by the follower spring 53 will cause the top staple 15 in the stack to be biased to a position between the rails where it will be engaged by one of the lugs 20 on the driver when the drive 18 is in its first position, and will be moved off of the stack 19 and along the track 16 as the driver 18 is moved toward its second position.

To operate the stapler 10, a user manually squeezes the major portion of the activating lever 34 toward the pistol grip 36, causing it to pivot at the pin 35 and, via its pin-like projection 37, to move the driver 18 from its first position (FIGS. 2, 3, 4 and 8) to its second position (FIGS. 6 and 10) against the bias of the main spring 40. Such movement of the driver 18 will cause the staples 15 disposed along the rails 17 to be slid toward the anvil 14 by engagement between the lugs 20 on the driver and those staples 15, including movement of the top staple 15 in the stack 19 being fed from the staple cartridge 46; with such engagement being ensured by movement of the planar surfaces 25 and 26 of the cam members 22 and 24 in engagement with each other to maintain the lugs 20 in engagement with the staples 15 along the rails 17 (FIG. 5). As the driver 18 approaches its second position, the leading staple 15 disposed on its end surface 32 will engage the anvil 14 and will be closed around the anvil 14 so that it may suture living tissue such as fascia disposed adjacent the anvil 14 (FIGS. 6 and 10). When the driver 18 reaches its second position, the lifting springs 30 will cause the end of the driver 18 to move transversely away from the track 16 (FIG. 6) which transverse movement, depending on the strength of the lifting springs 30, could occur immediately when the driver 18 reaches its second position so that the planar surfaces 25 and 26 of the cam members 22 and 24 separate, or could occur when the user of the stapler 10 releases at least part of the force applied through the driver 18 to close the leading staple 15 around the anvil 14. In either event, such transverse movement will slide the closed staple 15 off the distal end of the anvil 14. Upon subsequent movement of the driver 18 back toward its first position under the influence of the main spring 40, the second surface portion 27 of the cam member 22 on the second surface portion 27 of the cam member 22 on the driver 18 will slide over the second surface portion 28 on the cam members 24 on the guide plate 12 (FIG. 7), causing the lugs 20 on the driver 18 to move around the staples 15 along the rails 17 and back into engagement with subsequent staples 15 along the rails 17 as the driver returns to its first position. The stapler is then ready to be used again.

I claim:

1. In a stapling device for suturing tissues with metal staples including a frame, an anvil mounted on said frame, and means for moving a plurality of open staples along a track leading to said anvil and sequentially into engagement with said anvil to close the staple engaging the anvil comprising a driver mounted on said frame for movement along a predetermined path generally aligned with said track between first and second positions with said driver more closely adjacent said anvil in said second position, the improvement wherein said driver includes a plurality of fixed spaced lugs adapted to engage between staples spaced at predetermined distances along said track; and said stapler includes means adapted for engagement between said driver and said frame, including a cam member fixed on the driver and a cam member fixed on the frame, which cam members directly interact with each other, for affording positioning of said lugs in engagement with staples spaced at said predetermined distances along said track when said driver is in said first position and for causing said driver to advance the staples along the track and engage the leading staple with the anvil to close the leading staple during movement of said driver from said first to said second position, and for causing movement of said lugs out of engagement with the staples along the track, around, and into engagement with subsequent staples along said track during movement of said driver from its second position back to its first position.

2. A stapler according to claim 1 wherein said cam members on said driver and said frame have first surfaces shaped to engage and causing movement of the lugs of said driver along said track with said lugs in engagement with said staples during movement of said driver from its first to its second position, and have opposite second surfaces shaped to engage and move said driver around the staples along the track and then back to said track with the lugs in engagement with the subsequent staples along the track during movement of said driver from its second to its first position upon displacement of the cam member on said driver a small distance transversely away from said track at said second position; and said stapler includes lifting spring means between said frame and said driver for displacing said cam members said small distance when said driver is in said second position.

3. A stapler according to claim 1 wherein said track is provided by parallel elongate rails frictionally receiving end portions of said staples with said staples opening toward said anvil, said rails affording frictional sliding movement of said staples therebetween toward said anvil and said rails having an opening along one side to afford access to the staples along said rails by said lugs.

4. A stapler according to claim 3 wherein said stapler further includes means for feeding a stack of said staples in side-by-side relationship to the ends of said rails opposite said anvil with the staple in said stack at said rails opening toward said anvil.

5. A stapler according to claim 1 wherein said stapler further includes means for feeding a stack of said staples in side-by-side relationship to the end of said track opposite said anvil with the staple in said stack at said track opening toward said anvil.

6. A stapler according to claim 2 wherein said stapler further includes a second single spring means for biasing said driver to its first position, to a position with said lugs in engagement with said staples both in said first position and during movement of said driver from its first to its second position, and for biasing the second surfaces of said cam members into engagement with each other as said driver is moved from said second to said first position.

7. A stapler according to claim 2 wherein said staple driver is an elongate member having its end opposite said anvil guided on said frame along a path parallel to said track, said cam members are positioned near the end of said driver adjacent said anvil, said driver includes a pin projecting from the side of said driver opposite the direction of said displacement and said stapler includes a spring coupled between said frame and said pin to both bias said driver to said first position and provide a torque around the end of said driver opposite said anvil in all positions of said driver to bias said driver toward said track.

* * * * *